United States Patent [19]

Ebner

[11] Patent Number: 5,185,455
[45] Date of Patent: Feb. 9, 1993

[54] METHOD FOR IMPROVING THE PERFORMANCE OF VPO CATALYSTS

[75] Inventor: Jerry R. Ebner, St. Peters, Mo.

[73] Assignee: Monsanto Company, St. Louis, Mo.

[21] Appl. No.: 836,434

[22] Filed: Feb. 18, 1992

[51] Int. Cl.$^5$ .................. C07D 307/34; C07D 307/36
[52] U.S. Cl. .................................... 549/259; 549/262; 549/258
[58] Field of Search .................... 549/258, 259, 262

[56] References Cited

U.S. PATENT DOCUMENTS

| | | | |
|---|---|---|---|
| 3,474,041 | 10/1969 | Kerr | 252/411 |
| 4,515,899 | 5/1985 | Click et al. | 549/259 |
| 4,701,433 | 10/1987 | Edwards | 549/259 |
| 4,810,803 | 3/1989 | Edwards | 549/259 |

Primary Examiner—Cecilia Tsang
Attorney, Agent, or Firm—W. W. Brooks

[57] ABSTRACT

An improvement in a process for the manufacture of maleic anhydride by catalytic oxidation of n-butane in the presence of trimethyl phosphate over a fixed bed vanadium phosphorus oxide catalyst in a tubular reactor. The trimethyl phosphate content of the gas entering the reactor within a range of between about (0.9) N and about (1.1) N where N is a normative concentration of trimethyl phosphate in ppm as determined by the following relationship:

$$N + 5 \times C_4 + 6 \times (H_2O - 2.4) + 0.75 \times (CONV - c) + (SV/(25 \times P_{in}))$$

where:

$C_4 \times$ the mole % of n-butane in the gas entering the reactor;

$H_2O \times$ the mole % moisture in the gas entering the reactor;

$CONV \times$ % butane conversion in the reactor;

$SV \times$ gas hourly space velocity of the gas at the inlet of the reactor, reduced to one atmosphere pressure and 60° F.;

$P_{in} \times$ the pressure at the inlet of the reactor (psig); and $c \times 84 - 0.05[(SV \times C_4)/P_{in}]$;

Irrespective of the computation of N, the trimethyl phosphate content is at least about 1 ppm.

11 Claims, No Drawings

METHOD FOR IMPROVING THE PERFORMANCE OF VPO CATALYSTS

BACKGROUND OF THE INVENTION

This invention relates to the field of catalytic oxidation of hydrocarbons to produce oxygenated hydrocarbons and more particularly to a method for improving the control of a process for the preparation of maleic anhydride.

Conventionally, maleic anhydride is manufactured by passing a gas comprising n-butane and oxygen through a fixed catalyst bed tubular plug flow reactor containing a catalyst that consists of mixed oxides of vanadium and phosphorus. The catalyst may contain minor amounts of promoters or activators such as iron, lithium, zinc, chromium, uranium, tungsten, various other metals, boron and/or silicon. The oxidation reaction is highly exothermic. Conventionally a shell and tube heat exchanger is used as a reactor with the catalyst packed in the tubes through which the reactant gases are passed. A cooling fluid, typically molten salt, flows over the outsides of the tubes. Because the length to diameter ratio of the tubes is high, the reaction system approaches plug flow. The cooling capacity is substantially uniform throughout the reactor, but the rate of reaction varies widely with the concentration of hydrocarbon reactant and temperature. Because the reactant gases are normally introduced into the catalyst bed at a relatively low temperature, the reaction rate is low in the region immediately adjacent the inlet. However, once the reaction begins, it proceeds at a rapid pace which is accelerated by an increase in temperature resulting from the release of reaction heat. The temperature continues to increase with distance along the length of the reactor tube until a point is reached at which depletion of the hydrocarbon causes the rate of generation to slow, allowing the remainder of the reactor to operate at a lower temperature differential. Thus, a point of maximum temperature is reached, which is generally referred to as the "hot spot" of the reactor.

Problems occur in the operation of the reactor if the hot spot temperature becomes too high. In particular, the selectivity of the catalyst varies inversely with the reaction temperature while the rate of reaction varies directly. Thus, the higher and sharper the hot spot, the greater the proportion of n-butane feed that is consumed by reaction at high temperature and low selectivity. Yield of maleic anhydride may thus be adversely affected. Moreover, exposure of the catalyst bed to excessive temperatures tends to degrade the catalyst, reducing the productivity of the plant and, in some instances the inherent selectivity of the catalyst, i.e., the selectivity at a given reaction temperature. Moreover, because the reaction rate constant increases exponentially with temperature, reaction can run away if the gas temperature substantially exceeds a temperature 80° C. higher than the cooling fluid. Additionally, higher temperatures tend to favor the complete oxidation of the hydrocarbon to $CO_2$ and water. This not only reduces the yield and productivity of desired product, but higher heat of reaction released in conversion to $CO_2$ causes the problem to be compounded by further increasing the temperature.

It is known in the art to modulate catalyst activity and enhance selectivity by adding a small proportion of phosphorus compound to the feed gas entering the tubular reactor. Although the function of the phosphorus compound is not fully understood, it is believed that a portion of the phosphorus compound may be sorbed by the catalyst, thereby increasing or restoring the phosphorus/vanadium ratio in the catalyst to a level most favorable for catalyst selectivity. It is believed that phosphorus is lost from the catalyst composition under the catalytic oxidation conditions, and that addition of phosphorus compound may tend to restore the P/V ratio to a desired level which favors formation of maleic anhydride in preference to various by-products.

Incorporation of moisture in the feed gas to the maleic anhydride reactor is also known in the art. Again, the function of this additive is not entirely understood. However, it has been suggested among other things that the incorporation of moisture promotes a relatively even distribution of sorbed phosphorus compound throughout the catalyst bed. In the absence of moisture, it has been observed that the phosphorus compound added to the feed gas tends to deposit in a zone immediately adjacent the inlet to the tubular reactor.

Kerr U.S. Pat. No. 3,474,041 describes the addition of an organophosphorus compound for reactivation of mixed vanadium and phosphorus oxide catalyst for the oxidation of butane to maleic anhydride. Various means for introducing the organophosphorus compound into the catalyst bed are described, including introduction of the phosphorus compound into the butane and oxygen-containing feed gas to the reactor. Best results are said to be obtained by adding the organophosphorus compound after discontinuing hydrocarbon flow and blowing the reactivated catalyst with air prior to the reintroduction of hydrocarbon. A wide range of organophosphorus compounds are said to be useful in the Kerr process. Preferred phosphorus compounds are those wherein the phosphorus has a valence of less than +5, such as phosphines, phosphine oxides, phosphinites, phosphinite esters, the dialkyl phosphites, the trialkyl phosphites, the tetraalkylpyrophosphites, and mixtures thereof. The reference notes that the phosphorus compound can serve as a stabilizer as well as a reactivator for the catalyst.

Click et al. U.S. Pat. No. 4,515,899 describes steam regeneration of phosphorus treated vanadium/phosphorus/oxygen catalyst for maleic anhydride. The reference notes that the treatment of the catalyst with phosphorus compound reduces activity but increases selectivity, the loss of activity being compensated for by an increase in temperature of the reaction. This reference reports that, in practice, it is found that phosphorus compounds concentrate near the feed end of the reactor thus requiring that the amount of phosphorus addition be limited. Addition of steam after treatment with phosphorus compound redistributes the phosphorus compound more evenly through the reaction zone. In one embodiment the phosphorus compound treatment may be conducted over an extended period of time prior to the steam treatment, while in a second embodiment the phosphorus compound treatment and steam treatment may be substantially contiguous, that is the steam treatment follows immediately after each phosphorus treatment. Among the preferred phosphorus compounds used in the Click et al. process are trimethyl phosphite and trimethyl phosphate.

Edwards U.S. Pat. No. 4,701,433 applies both water and phosphorus compound in situ in amounts sufficient to partially deactivate a portion of the catalyst. Edwards teaches that addition of the combination of phosphorus compound and water serves to deactivate the region in which the hot spot of the reaction occurs, thereby moving the hot spot downstream and apparently allowing for reactivation of the region in which the hot spot previously occurred. Use of both phosphorus compound and water also makes the temperature profile of the reactor more isothermal, which further increase maleic anhydride yield. A similar disclosure is contained in Edwards U.S. Pat. No. 4,810,803. Both references disclose the use of alkyl phosphites and alkyl phosphates, including trimethyl phosphate, for treatment of the catalyst bed.

Although the beneficial effect on catalyst selectivity and catalyst life which results from incorporating phosphorus compound in the maleic anhydride reactor feed is well known, the literature available to the art has not closely identified the amounts of particular phosphorus compounds which are most advantageously used. If an excessive proportion of phosphorus compound is included in the reactor feed, not only is an excessive cost incurred in the consumption of phosphorus compound but the activity of the catalyst is unnecessarily decreased and yields are adversely affected. Determination of the appropriate concentrations of trimethyl phosphate in the feed gas to the maleic anhydride reactor is complicated where water is also included in the feed gas. Thus, there has been an unsatisfied need in the art for a method for controlling phosphorus compound addition to achieve the substantial benefits thereof without unnecessary sacrifice of productivity or yield.

SUMMARY OF THE INVENTION

Among the several objects of the present invention, therefore, may be noted the control of reaction conditions to enhance catalyst selectivity in a process for the production of maleic anhydride by catalytic oxidation of n-butane over a phosphorus/vanadium/oxide catalyst; the control of reaction conditions in such process to prolong catalyst life; the control of conditions in such process to promote high productivity and high yield; and the provision of such a process in which the temperature profile of the reactor is controlled to minimize the temperature peak at the hot spot, thereby contributing to high selectivity, high productivity and high yield.

It is a more particular object of the present invention to control the rate of addition of phosphorus compound to the n-butane and oxygen stream entering a maleic anhydride reactor to provide high selectivity without excessive use of phosphorus compound or unnecessarily deleterious effect on the activity of the catalyst.

Briefly, therefore, the present invention is directed to an improvement in a process for the manufacture of maleic anhydride by passing through a tubular reactor a gas initially containing n-butane, oxygen, and trimethyl phosphate in which the tubular reactor contains a fixed bed of a catalyst comprising vanadium, phosphorus, and oxygen, and in which n-butane and oxygen react to produce maleic anhydride in the vapor phase. In accordance with the improvement, the trimethyl phosphate content of the gas entering the tubular reactor is controlled within a range of concentration that is between about (0.9)N and about (1.1)N wherein N is a normative concentration of trimethyl phosphate in ppm as determined by the following relationship.

$$N = 5 \times C_4 + 6 \times (H_2O - 2.4)0.75 \times (CONV - c) + (SV/(25 \times P_{in}))$$

where:

$C_4$ = the mole % of n-butane in the gas entering the reactor;

$H_2O$ = the mole % moisture in the gas entering the reactor;

CONV = % butane conversion in the reactor;

SV = gas hourly space velocity of the gas at the inlet of the reactor, reduced to one atmosphere pressure and 60° F.;

$P_{in}$ = the pressure at the inlet of the reactor (psig); and
$c = 84 - 0.05[(SV \times C_4)/P_{in}]$.

However, irrespective of the above computation of N, the trimethyl phosphate concentration is at least about 1 ppm.

Other objects and features will be in part apparent and in part pointed out hereinafter.

DESCRIPTION OF THE PREFERRED EMBODIMENTS

In accordance with the invention, it has been discovered that an optimum or near optimum effect on productivity of the catalytic oxidation of n-butane to maleic anhydride is achieved by addition of trimethyl phosphate in a defined range of proportions in the gas entering the catalytic reactor. Generally, it has been learned that, as butane concentration in the feed gas to the reactor and space velocity increase, or pressure decreases, the target conversion of butane should be reduced to maintain the best possible yields. Selectivity and yields are enhanced by the incorporation of a phosphorus compound, preferably trimethyl phosphate, in the gas entering the reactor. Most preferably, a combination of trimethyl phosphate and water vapor are incorporated in the gas that enters the reactor.

More particularly, it has been found that, in a preferred range of operating conditions, the most effective operation is achieved when the trimethyl phosphate content of the gas entering the reactor is between about (0.9)N and (1.1)N where N is a normative proportion of trimethyl phosphate determined in accordance with the relationship:

$$N = 5 \times C_4 + 6 \times (H_2O - 2.4)0.75 \times (CONV - c) + (SV/(25 \times P_{in}))$$

where $C_4$ = the mole % of n-butane in the gas entering the reactor;

$H_2O$ = the mole % moisture in the gas entering the reactor;

CONV = % butane conversion in the reactor;

SV = gas hourly space velocity of the gas at the inlet of the reactor, reduced to one atmosphere pressure and 60° F.

$P_{in}$ = the pressure at the inlet of the reactor (psig); and
$c = 84 \times 0.05 [(SV \times C_4/Pin)]$.

Under certain relatively unusual combinations of conditions, the above algorithm may yield a value of N that is very low, possibly even negative. It has been found that, irrespective of the computation of N, the trimethyl phosphate content should be maintained at at least about 1 ppm. Thus, the trimethyl phosphate content is the greater of 1 ppm and a value of between about (0.9)N and about (1.1)N.

The above relationship has been found to identify an especially advantageous range of trimethyl phosphate dosage for operations within preferred ranges of n-butane concentration in the feed gas, temperatures in the reactor system, conversion, and other variables. The rate of introduction of hydrocarbon into the catalyst bed is controlled so that the conversion of hydrocarbon is at least about 65% in a single pass, and the temperature differential between the gas and the cooling fluid does not exceed about 80° C. anywhere within the catalyst bed. The reaction temperature may vary from about 350° C. to about 510° C. Generally a salt bath is used as a cooling fluid outside the tubes that contain the catalyst and the temperature of the salt bath is maintained in the range of between about 340° and about 460° C. preferably between about 400° and 450° C. The rate of hydrocarbon introduction is controlled by varying the initial concentration of hydrocarbon, the space velocity, or both. Preferably, the hydrocarbon content of the inlet gas is between about 1% by volume and about 4% by volume. Space velocities are preferably in the range of between about 750 to about 4,000 h$^{-1}$, more preferably between about 1,000 to about 3,000 h$^{-1}$. Since lower pressures and higher space velocities limit the maximum feasible C$_4$ concentration, and vice versa, it is useful to consider the product of these two parameters expressed in the form of a "gas loading factor" which is defined mathematically as follows.

$$GLF = (SV \times C_4)/P_{in}$$

where GLF is the gas loading factor and SV, C$_4$ and P$_{in}$ are as defined above.

Preferably, the gas loading factor is between about 15 and about 350% C$_4$/psig-hr, more preferably between about 90 and about 275% C$_4$/psig-hr. The pressure may range from about $1.0 \times 10^2$ kPa gauge (15 psig) to about $3.45 \times 10^2$ kPa gauge (50.0 psig), more preferably from about $1.0 \times 10^2$ to about $2.75 \times 10^2$ kPa gauge (15 to 40 psig).

The above relationship was developed based on observations of operations using a catalyst represented by the formula $$(VO)_2(M)_m P_2 O_7 \cdot b(P_2/_c O)$$

wherein M is a promoter element, m is a number from 0 to about 0.2, b is a number taken to provide a P/V atom ratio of from about 1.0 to about 1.3 and, c is a number representing the oxidation number of phosphorus and has a value of 5. Promoter elements which can constitute M include essentially any of the elements from groups IA, IB, IIA, IIB, IIIA, IIIB, IVA, IVB, VA, VB, VIA, VIB, and VIIIA of the periodic table of the elements.

Such catalysts are prepared by transformation of a catalyst precursor represented by the formula $$VO(M)_m HPO_4 \cdot a H_2 O \cdot b(P_2/_c O) \cdot n(\text{organics})$$

wherein M, m, b, and c are defined above, a is a number of at least about 0.5, and n is a number taken to represent the weight % of intercalated organic components. In preparation of the catalyst, the precursor is heated in air, steam, an inert gas, or mixtures thereof to a temperature not exceeding about 300° C. The catalyst precursor is maintained at such temperature under an atmosphere containing molecular oxygen, steam and optionally an inert gas represented by the formula $$(O_2)_x (H_2 O)_y (IG)_z$$

wherein IG is an inert gas and x, y, and z represent the respective mole percentages of O$_2$, H$_2$O, and IG components, respectively, in the molecular oxygen/steam containing atmosphere. The parameter x has a value greater than 0 mole % but less than 100 mole %, y has a value greater than 0% and less than 100 mole % and z has a value representing the balance of the molecular oxygen/steam containing atmosphere. The temperature is thereafter increased at a programmed rate of from about 2° C. per minute to about 12° C. per minute to a value effective to eliminate the water of hydration from the catalyst precursor. Thereafter, the temperature is adjusted to a value greater than 350° C. but less than 550° C. and the phosphorus/vanadium oxide composition maintained at the latter temperature in the molecular oxygen/steam containing atmosphere for a time effective to provide a vanadium oxidation state from about +4.0 to about +4.5. The composition is thereafter maintained at such temperature in a non-oxidizing steam containing atmosphere for a time effective to complete the transformation of the catalyst precursor to active catalyst. The process of preparation of the catalyst is more fully described in the co-pending and co-assigned application Ser. No. 07/722,070 filed Jun. 27, 1991, expressly incorporated herein by reference.

To realize the maximum benefit from control of the rate of trimethyl phosphate addition within the range of 0.9N to 1.1N as determined from the above defined relationship, it is important to maintain the addition rate within such range in sustained operations over an extended period of time. The benefit is not lost by occasional short-term excursions from this addition rate; but it is preferred, for example, that the addition rate be controlled so that the concentration of trimethyl phosphate in the gas entering the reactor is controlled between about 0.9N and about 1.1N for at least 80% of the reactor operating time over a period of at least about six months, more preferably at least one year, of substantially continual operation. Most preferably, the concentration is maintained within the aforesaid range for at least 80% of the reactor operating time substantially over the life of the catalyst.

Adjustments of the trimethyl phosphate addition rate can be made manually based on determinations of the mole % n-butane in the gas entering the reactor, the n-butane conversion, the moisture content of the gas entering the reactor, the gas hourly space velocity, and the pressure of the gas entering the reactor. Those skilled in the art will be familiar with the measurements of flow rate, temperature, pressure and concentration that are necessary for these determinations. For example, measurements might be made on the temperature, pressure, moisture content, n-butane concentration and volumetric flow rate of both the gas entering the reactor and the gas leaving the reactor. Together with information on the volume of the catalyst bed, these measurements allow the ready calculation of the mole % n-butane in the feed, butane conversion, and gas hourly space velocity. Using the above relationship, N can be calculated, and the rate of addition of trimethyl phosphate adjusted as required to maintain the trimethyl phosphate concentration in the above specified range.

In a preferred embodiment of the invention, the rate of addition of trimethyl phosphate is controlled automatically using a computer programmed to compute N in accordance with the aforesaid relationship. Measurements are made of various parameters from which determinations may be made of the mole % n-butane in the gas entering the reactor, the moisture content of the gas entering the reactor, the % conversion of n-butane in the reactor, the hourly gas space velocity, and the pressure entering the reactor. Typically, the measurements made are those discussed above in connection with manual control of the rate of addition of trimethyl phosphate. Parameters are also measured from which a determination may be made of either the rate of addition of trimethyl phosphate to the gas entering the reactor, or the trimethyl phosphate content of the gas entering the reactor. Signals are generated reflecting the various parameters that are measured, and those signals are transmitted to a computer that is programmed to make the computation of N. Optionally, the computer may also be programmed to calculate the rate of addition of trimethyl phosphate necessary so that the trimethyl phosphate content of the gas entering the reactor is equal to N.

The computer makes a comparison to determine whether the rate of trimethyl phosphate addition is within the desired range. According to one embodiment, the computer compares the determined rate of addition of trimethyl phosphate entering the reactor with the calculated rate necessary for the trimethyl phosphate content of the gas entering the reactor to be equal to N. An error signal is generated reflecting any difference between the determined rate of addition and the calculated rate of addition. This error signal is transmitted to a flow controller or other means for controlling the rate of addition of trimethyl phosphate. A signal from the flow controller is transmitted to an automatic valve in a trimethyl phosphate supply line, or valve positioner on such valve, and thereby causes the rate of addition of trimethyl phosphate to be adjusted to the desired value, or within the desired range In an alternative embodiment, the trimethyl phosphate content of the gas is determined after the point of trimethyl phosphate addition, and the computer compares the determined trimethyl phosphate content of the gas entering the reactor with N. Again an error signal is generated reflecting any difference. This error signal is transmitted to an automatic valve or valve positioner, thereby causing the rate of addition of trimethyl phosphate to be adjusted to a level at which the error signal is reduced to zero, or to an acceptable maximum.

Although the above algorithm was derived from data on a pilot plant tubular reactor, the data obtained reflects basic relationships that are generally transferable to commercial maleic anhydride reactors operating within the ranges of conditions outlined above. However, the precise optimum concentration may vary slightly from N as determined from the algorithm. Such slight difference in optimum TMP concentration may arise from variations between the pilot plant reactor and commercial fixed bed reactors with respect to heat transfer characteristics, cooling fluid side flow rates, flow patterns, tube scaling, exact tube dimensions, inlet piping configurations, gas residence time, and other parameters for which there is not an exact one to one correspondence between the pilot plant and the commercial reactor.

Further in accordance with the invention, therefore, evolutionary operation (EVOP) techniques may be employed to account for the peculiarities of a particular reactor and correct the computation of N to a concentration more near the absolute optimum for such system. Ordinarily, the absolute optimum for a commercial reactor is very closely approached by using EVOP to determine a single correction term (dN) by which N may be adjusted algebraically. To determine the adjustment term by EVOP, a commercial plant reactor is initially run at a base line TMP concentration N that is preferably within a range of N±5%, more preferably within N±1%. At the initial TMP concentration, data are gathered as a function of time for significant indicative parameters of the system, preferably including, for example, hot spot temperature, hot spot location, temperature difference between cooling fluid and reaction gas, and yield. TMP concentration is maintained within the initial range for a time sufficient to establish statistically significant averages and trends, typically at least about five days. The TMP concentration is then varied between the limits of a second range, for example N±10%, which is sufficiently broader than the initial range to yield data on the indicative parameters from which statistically significant differences from the initial range averages and trends can be identified within a reasonably EVOP period, for example, 5 to 10 days. After a period of operation within the second range, the TMP concentration is advantageously varied between the limits of a third range, for example N±20%, which is sufficiently broader than the second range to identify further statistically significant differences between the second and third range averages and trends within a reasonably EVOP period, again typically 5 to 10 days. Further stages of EVOP operation may be followed if desired, using increasingly broader ranges of TMP concentration. With each change of TMP concentration, data are taken as a function time for the indicative parameters. Using EVOP statistical methods known to the art, a correction term dN may be determined for the algorithm so as to obtain maximum Yield with a minimum hot spot peak temperature, minimum temperature difference between reaction gas and cooling fluid, and location of the hot spot within the first 60% of the catalyst bed length in the tubular reactor.

Those skilled in the art will readily recognize variations in the specific protocols which may be used in EVOP determinations. As an alternative to determining a single correction term dN, closer fine tuning of the process can be realized by using EVOP techniques and processing the data to identify correction terms or factors for the individual coefficients of the algorithm. However, for commercial purposes, a simple correction for N by dN ordinarily achieves all or nearly all of the economically significant refinement of the method of the invention for optimizing TMP content.

EXAMPLE 1

A 12 liter flask fitted with a paddle stirrer, a thermometer, a heating mantle, and a reflux condenser was charged with isobutyl alcohol (9,000 ml), oxalic acid (378.3 gm), and $V_2O_5$ (848.4 gm). Phosphoric acid (105.7% $H_3PO_4$; 997.6 gm) was thereafter added to the flask. The resulting mixture was refluxed for about 16 hours, yielding a bright blue reaction mixture. Approximately one-fourth of the alcohol solvent was stripped from this mixture, after which the residue in the reactor was cooled and half of the remaining solvent was decanted to produce a concentrated slurry. The slurry was quantitatively transferred to a flat dish and dried at a temperature between 110° C. and 150° C. in nitrogen. The dried material was then optionally further dried by heating in air at 250° to 260° C. for several hours to yield a gray-black VPO catalyst precursor powder. The VPO precursor powder prepared in this manner had a P/V ratio of 1.08±0.05.

Using a Stokes 512 rotary tabletting machine equipped with needed dyes and punches, a VPO precursor powder prepared in the above fashion was formed into various catalyst bodies. These bodies were then processed in a box oven with the following protocol of temperature and gas composition. The catalyst bodies were heated in air or nitrogen to 250° C. as the starting temperature for ramp heating. An oven heat-up was then conducted from 250° C. to 425° C. at a controlled rate of 4° C. per minute in an atmosphere of 50% air and 50% steam. The catalyst bodies were thereafter maintained at 425° C. for one hour under the aforesaid 50% air/50% steam atmosphere. After this one hour hold, the gas atmosphere was changed to 50% nitrogen and 50% steam and the catalyst bodies were maintained at 425° C. for an additional six hours, after which they were cooled.

EXAMPLE 2

Various catalysts prepared generally in the manner described in Example 1 were tested for efficiency in terms of reaction yield of maleic anhydride from n-butane using butane feed compositions containing varying levels of trimethyl phosphate. In each test, the catalyst bodies were charged to a 2.10 cm inside diameter by 600 cm long fixed bed tubular reactor and the butane oxidation reaction conducted for hundreds of hours of on-stream time. Two series of test reactions were conducted. In a test series designated C2770, the catalyst bed was arranged as follows, measuring longitudinally from the reactor inlet: 2" of aluminum inerts; 49" of 5/32" diameter trilobe; 60" of ¼" diameter trilobe; and 118" of 5/32" diameter trilobe. In a series designated C2754, the reactor contained 2" of aluminum inerts, followed by 30" of 5/32" trilobes, 62" of ¼" trilobes, and 114" of 5/32" trilobes. In each test reaction the catalyst was brought on-stream at a low butane concentration which was increased to 2.4 mole % butane over the first several hundred hours of operation. The data set forth in Table 1 illustrate the results of operating the catalyst using feed gas having a TMP concentration within and outside the range of (0.9)N to (1.1)N as computed according to the algorithm set forth hereinabove. When the water level in the incoming air changes, as is common with changing weather conditions, deleterious performance effects are observed, as shown in Table 1. However, such deleterious performance effects can be reduced substantially if the TMP level is adjusted appropriately. Thus, the data in Table 1 illustrate that operating outside the appropriate range of TMP concentration lowers reaction yields and results in higher hot spot temperature peaks and larger temperature differentials between the reacting gases and the cooling fluid (salt bath). It is known in the art that high hot spot temperatures can harm both short- and long-term catalyst performance and should, therefore, be minimized during operation of a maleic anhydride catalytic reactor. As further shown in Table 1, when the TMP levels are restored to within the prescribed algorithm values, stable high performance is again restored. It is thus demonstrated that rapid adjustment of trimethyl phosphate level to reflect prevailing reaction conditions will maximize the on-stream time at the highest catalyst performance level.

TABLE 1

| EXP | OST HRS | INLET P PSIG | SV HR-1 | % C4 | % H2O | BATH (°C.) | HOT SPOT (°C.) | DELTA (HS-B) | % CONV | % YIELD |
| --- | --- | --- | --- | --- | --- | --- | --- | --- | --- | --- |
| C2770 | | | | | | | | | | |
| A | 908 | 31.1 | 1625 | 2.39 | 2.4 | 416 | 447 | 31 | 83 | 60.7 |
|  | 945 | 31.1 | 1625 | 2.4 | 2.4 | 416 | 448 | 32 | 82.4 | 60 |
|  | 969 | 31.1 | 1625 | 2.4 | 2.4 | 416 | 447 | 31 | 82.1 | 60.6 |
| B | 1031 | 31.1 | 1625 | 2.4 | 4 | 416 | 476 | 60 | 83.3 | 57.8 |
|  | 1064 | 31.2 | 1624 | 2.4 | 4 | 416 | 483 | 67 | 82.5 | 58.4 |
| C | 1174 | 30.9 | 1628 | 2.4 | 4 | 422 | 457 | 35 | 83.5 | 60.8 |
|  | 1225 | 31 | 1628 | 2.4 | 4 | 422 | 457 | 35 | 83.7 | 59.9 |
|  | 1284 | 31 | 1628 | 2.39 | 4 | 423 | 458 | 35 | 83.8 | 60 |
|  | 1344 | 31.1 | 1628 | 2.4 | 4 | 422 | 461 | 39 | 83.1 | 59.9 |
| C2754 | | | | | | | | | | |
| A | 1514 | 30.9 | 1627 | 2.4 | 5 | 417 | 493 | 76 | 84.3 | 57.7 |
| | | | FINAL DATA POINT PRIOR TO HOT SPOT RUNAWAY | | | | | | | |
| B | 1604 | 30.8 | 1627 | 2.4 | 1.2 | 415 | 444 | 29 | 83.6 | 58.9 |
| C | 1672 | 30.9 | 1625 | 2.4 | 0.2 | 407 | 483 | 76 | 83.5 | 55 |

| EXP | PROD | TMP ACTUAL | N = TMP CALC. | TMP RANGE 0.9 N | 1.1 N | GLF |
| --- | --- | --- | --- | --- | --- | --- |
| C2770 | | | | | | |
| A | 6.12 | 17 | 17.8 | 16.0 | 19.6 | 125 |
|  | 6.05 | 17 | 17.4 | 15.7 | 19.2 | 125 |
|  | 6.1 | 17 | 17.2 | 15.5 | 18.9 | 125 |
| B | 5.82 | 17 | 27.7 | 24.9 | 30.5 | 125 |
|  | 5.88 | 20 | 27.1 | 24.4 | 29.8 | 125 |
| C | 6.13 | 28 | 27.9 | 25.1 | 30.7 | 126 |
|  | 6.04 | 28 | 28.1 | 25.2 | 30.9 | 126 |
|  | 6.04 | 28 | 28.1 | 25.3 | 30.9 | 126 |
|  | 6.01 | 28 | 27.6 | 24.8 | 30.3 | 126 |
| C2754 | | | | | | |
| A | 5.83 | 8 | 34.5 | 31.1 | 38.0 | 126 |
| | FINAL DATA POINT PRIOR TO HOT SPOT RUNAWAY | | | | | |
| B | 5.92 | 11 | 11.2 | 10.1 | 12.3 | 127 |
| C | 5.54 | 8 | 5.1 | 4.6 | 5.6 | 126 |

EXAMPLE 3

Further catalysts structures were prepared in the manner generally described in Example 1 and tested according to the method generally described in Example 2. In the test reactions of this Example, the catalyst was placed in the reactor in the following manner, measuring distances from the reactor inlet: 2" of alumina inerts, 48" of 5/32" diameter trilobes, 60" of ¼" diameter trilobes, and 118" of 5/32" inch diameter trilobes. The results of the tests in this Example are set forth in Table 2. The data of Table 2 further illustrate the results of the running the catalyst in and outside the range of 0.9N to 1.1N at process conditions that are essentially otherwise unchanged. When the TMP level is adjusted in accordance with the algorithm, lower hot spots, smaller temperature differentials, and better reaction yields are evidenced.

TABLE 2

| EXP | OST HRS | INLET P PSIG | SV HR-1 | % C4 | % H2O | BATH (°C.) | HOT SPOT (°C.) | DELTA (HS-B) | % CONV | % YIELD |
|---|---|---|---|---|---|---|---|---|---|---|
| A | 481 | 31 | 1626 | 2.4 | 3 | 422 | 461 | 39 | 83.8 | 58.3 |
|   | 484 | 31 | 1626 | 2.4 | 3 | 422 | 465 | 43 | 84.5 | 59.7 |
| B | 631 | 31 | 1626 | 2.4 | 3 | 420 | 478 | 58 | 83.6 | 56.3 |
|   | 636 | 31 | 1630 | 2.39 | 3 | 419 | 478 | 59 | 83.8 | 56.1 |

| EXP | TMP PROD | TMP ACTUAL | N = TMP CALC. | TMP RANGE 0.9 N | 1.1 N | GLF |
|---|---|---|---|---|---|---|
| A | 5.86 | 21 | 22.1 | 19.9 | 24.3 | 126 |
|   | 6.02 | 21 | 22.6 | 20.4 | 24.9 | 126 |
| B | 5.68 | 17 | 22.0 | 19.8 | 24.2 | 126 |
|   | 5.65 | 17 | 22.1 | 19.9 | 24.3 | 126 |

What is claimed is:

1. In a process for the manufacture of maleic anhydride by passing through a tubular reactor a gas initially containing n-butane, oxygen, and trimethyl phosphate, said tubular reactor containing a fixed bed of a catalyst comprising vanadium, phosphorus, and oxygen in which n-butane and oxygen react to produce maleic anhydride in the vapor phase, the improvement which comprises controlling the trimethyl phosphate content of the gas entering said tubular reactor within a range of concentration that is between about (0.9)N and about (1.1)N where N is a normative concentration of trimethyl phosphate in ppm as determined by the following relationship:

$$N = 5 \times C_4 + 6 \times (H_2O - 2.4) + 0.75 \times (CONV - c) + (SV/(25 \times P_{in}))$$

where:
$C_4$ = the mole % of n-butane in the gas entering the reactor;
$H_2O$ = the mole % moisture in the gas entering the reactor;
CONV = % butane conversion in the reactor;
SV = gas hourly space velocity of the gas at the inlet of the reactor, reduced to one atmosphere pressure and 60° F.;
$P_{in}$ = the pressure at the inlet of the reactor (psig); and
$c = 84 \times 0.05 [(SV \times C_4)/Pin]$;
provided, however, that said trimethyl phosphate content is at least about 1 ppm.

2. An improved process as set forth in claim 1 wherein the concentration of trimethyl phosphate in the gas entering the reactor is controlled at between about (0.9)N and about (1.1)N for at least 80% of the reactor operating time over a period of at least about six months of substantially continual operation.

3. An improved process as set forth in claim 2 wherein the concentration of trimethyl phosphate in the gas entering the reactor is controlled at between about (0.9)N and about (1.1)N for at least 80% of the reactor operating time over a period of at least about one year of substantially continual operation.

4. An improved process as set forth in claim 3 wherein the concentration of trimethyl phosphate in the gas entering the reactor is controlled at between about (0.9)N and about (1.1) N for at least 80% of the reactor operating time substantially over the life of the catalyst.

5. An improved process as set forth in claim 1 wherein trimethyl phosphate is added to the gas entering said reactor, the addition of trimethyl phosphate being controlled by:
determining the mole % n-butane in the gas entering the reactor, the % conversion of n-butane in the reactor, the moisture content of the gas entering the reactor, said gas hourly space velocity, and said pressure; and
adding trimethyl phosphate to said feed gas at a rate sufficient to maintain the trimethyl phosphate content of the gas entering said reactor at between about (0.9)N and about (1.1)N.

6. An improved process as set forth in claim 5 further comprising the steps of:
measuring parameters from which determinations may be made of the rate of trimethyl phosphate addition to the gas entering the reactor, the mol % n-butane in the gas entering the reactor, the % of conversion of n-butane in the reactor, the moisture content of the gas entering the reactor, said gas hourly space velocity, and said pressure;
generating signals reflecting said measurements;
transmitting said signals to a computer that is programmed to compute N in accordance with said relationship, to calculate the rate of trimethyl phosphate addition required so that the trimethyl phosphate content of the gas entering the reactor is N, and to generate an error signal reflecting the difference between the actual rate of trimethyl phosphate addition and the rate required to maintain said trimethyl phosphate content equal to N;
transmitting said error signal to a means for controlling the rate of addition of trimethyl phosphate into the gas entering the reactor; and
adjusting said means as required to control the rate of addition of trimethyl phosphate to the gas entering said reactor so that the proportion of trimethyl phosphate in the gas entering said reactor is between about (0.9)N and about (1.1)N.

7. An improved process as set forth in claim 5 further comprising the steps of:
measuring parameters from which determinations may be made of the mol % n-butane in the gas entering the reactor, the % conversion of n-butane in the reactor, the moisture content of the gas entering the reactor, the trimethyl phosphate content of the gas entering the reactor, said gas hourly space velocity, and said pressure; said trimethyl phosphate content being measured at a point following addition of trimethyl phosphate;

generating signals reflecting said measurements;

transmitting said signals to a computer that is programmed to compute N in accordance with said relationship and to generate an error signal reflecting the difference between the determined trimethyl phosphate content of the gas entering the reactor and the trimethyl phosphate content equal to N;

transmitting said error signal to a means for controlling the rate of addition of trimethyl phosphate into the gas entering the reactor; and adjusting said means as required to control the rate of addition of trimethyl phosphate to the gas entering said reactor so that the trimethyl phosphate content of the gas entering said reactor is between about (0.9)N and about (1.1)N.

8. An improved process as set forth in claim 1 wherein said catalyst composition corresponds to the formula $$(VO)_2(M)_m P_2O_7 \cdot b(P_{2/c}O)$$

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, and b is a number taken to provide a P/V atom ratio of from about 1.0 to about 1.3, c is a number representing the oxidation number of phosphorus and has a value of 5, said catalyst having been prepared by transforming a catalyst precursor represented by the formula $$VO(M)_m HPO_4 \cdot aH_2O \cdot b(P_{2/c}O) \cdot n(organics)$$

wherein M, m, b, and c are as defined above, a is a number of at least about 0.5, and n is a number taken to represent the weight % of intercalated organics component, said transformation being effected by:

(a) heating the catalyst precursor in an atmosphere selected from the group consisting of air, steam, inert gas, and mixtures thereof to a temperature not to exceed about 300° C.;

(b) maintaining the catalyst precursor at the temperature of Step (a) and providing an atmosphere containing molecular oxygen, steam, and optionally an inert gas, the atmosphere being represented by the formula $$(O2)_x(H20)_y(IG)_z$$

wherein IG is an inert gas and x, y, and z represent mol percent of the O2, H20, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature at a programmed rate of from about 2° C./min to about 12° C./min to a value effective to eliminate the water of hydration from the catalyst precursor;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and (e) continuing to maintain the adjusted temperature in a nonoxidizing, steam-containing atmosphere for a time effective to complete the catalyst precursor-to-active catalyst transformation to yield the active catalyst.

9. A process as set forth in claim 8 wherein the n-butane content of the gas entering the reactor is between about 1% and about 4% by volume, the space velocity in the reactor is between about 750 and about 4,000 hr$^{-1}$, and the pressure is between about $1.0 \times 10^2$ and about $3.45 \times 10^2$ kPa gauge.

10. A process as set forth in claim 9 wherein the gas loading factor in the reactor is between about 15 and about 350% C$_4$/psig-hr.

11. A process as set forth in claim 1 wherein evolutionary operation techniques are employed to account for the peculiarities of a particular reactor and correct the computation of N to a concentration more near the absolute optimum for such system.

* * * * *